United States Patent
Gall et al.

(10) Patent No.: US 6,207,382 B1
(45) Date of Patent: Mar. 27, 2001

(54) PRODUCTION OF LAMPBRUSH CHROMOSOME

(75) Inventors: Joseph G. Gall; Christine V. Murphy, both of Baltimore, MD (US)

(73) Assignee: Carnegie Institution of Washington, Washington, DC (US)

( * ) Notice: Subject to any disclaimer, the term of this patent is extended or adjusted under 35 U.S.C. 154(b) by 0 days.

(21) Appl. No.: 09/192,187

(22) Filed: Nov. 16, 1998

Related U.S. Application Data

(60) Provisional application No. 60/066,103, filed on Nov. 17, 1997.

(51) Int. Cl.[7] .............................. C12Q 1/68; C12P 19/34; A61K 35/12
(52) U.S. Cl. ............................... 435/6; 435/91; 435/806; 435/810; 424/520
(58) Field of Search ................................. 435/6, 91, 806, 435/810; 424/520

(56) References Cited

U.S. PATENT DOCUMENTS

| | | | | |
|---|---|---|---|---|
| 5,358,847 | * | 10/1994 | Brown | 435/6 |
| 5,651,992 | * | 7/1997 | Wangh | 424/520 |

FOREIGN PATENT DOCUMENTS

95/21860    8/1995    (WO).

OTHER PUBLICATIONS

Montag et al., "In vitro Decondensation of Mammalian Sperm and Subsequent Formation of Pronuclei–Like Structures for Micromanipulation", Molecular Reproduction and Development, vol. 33, 1992, pp. 338–346, XP–00209706.

Gurdon, Injected Nuclei in Frog Oocytes: Fate, Enlargement, and Chromatin Dispersal, Journal of Embryology and Experimental Morphology, vol. 36, 1976, pp. 523–540, XP–002097751.

Gall et al., "Assembly of Lampbrush Chromosomes from Sperm Chromatin", Molecular Biology of the Cell, vol. 9, Apr. 1998, pp. 733–747, XP–002097707.

Gall et al., "Lampbrush Chromosomes from Xenopus Sperm Chromatin", Molecular Biology of the Cell (Abstracts), vol. 8, No. Suppl, 13–17 Dec. 1997, p. 4A, XP–002097705.

Lohka et al., "Formation in vitro of sperm pronuclei and mitotic chromosomes induced by amphibian ooplasmic components," Science, 1983, 220:719–721.

Lohka et al., "Roles of cytosol and cytoplasmic particles in nuclear envelope assembly and sperm pronuclear formation in cell–free preparations from amphibian eggs," Journal of Cell Biology, 1984, 98:1222–1230.

Kirschner et al., "The timing of early developmental events in Xenopus," Trends in Genetics, 1995, 1:41–47.

Almouzni et al., "Nuclear assembly, structure, and function: The use of Xenopus in vitro systems," Experimental Cell Research, 1993, 205:1–15.

Hausen et al., "The early development of *Xenopus laevis*," Springer–Verlag, New York, 1991, pp. 6 and 10, plate 9 and legend.

\* cited by examiner

*Primary Examiner*—Jeffrey Fredman
*Assistant Examiner*—Arun K. Chakrabarti
(74) *Attorney, Agent, or Firm*—Pillsbury Madison & Sutro, LLP

(57) ABSTRACT

A process for inducing a transcriptionally active chromosome (i.e., a "lampbrush" chromosome) from condensed chromatin or nucleus is disclosed. The condensed chromosome is contacted with the contents of a germinal vesicle. Preferably, the nuclear envelope is disrupted or removed. Moreover, a heterologous system of chromosome and germinal vesicle derived from organisms of different species is preferred because it permits analysis of organisms that do not have lampbrush chromosomes or cannot be manipulated by other techniques. Such lampbrush chromosomes can be attached to a substrate, and then analyzed by a variety of molecular and cytological techniques such as, for example, antibody detection of chromosomal protein, autoradiography, electron and light microscopy, histochemistry, image analysis, immunofluorescence, in situ hybridization of nucleic acids, morphology, and the like.

27 Claims, 10 Drawing Sheets

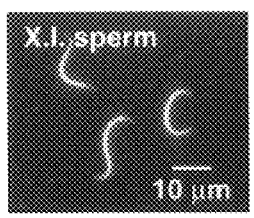  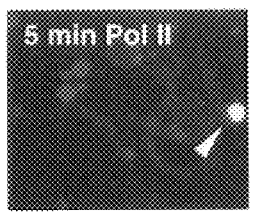 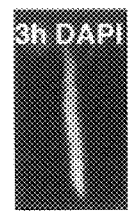 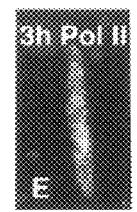
FIG. 1A  FIG. 1B  FIG. 1C  FIG. 1D  FIG. 1E
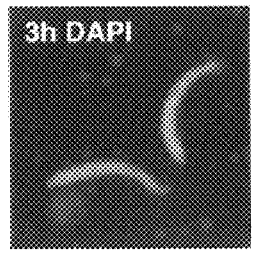 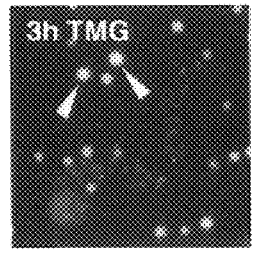 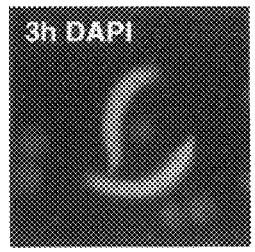 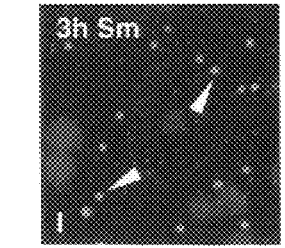
FIG. 1F  FIG. 1G  FIG. 1H  FIG. 1I

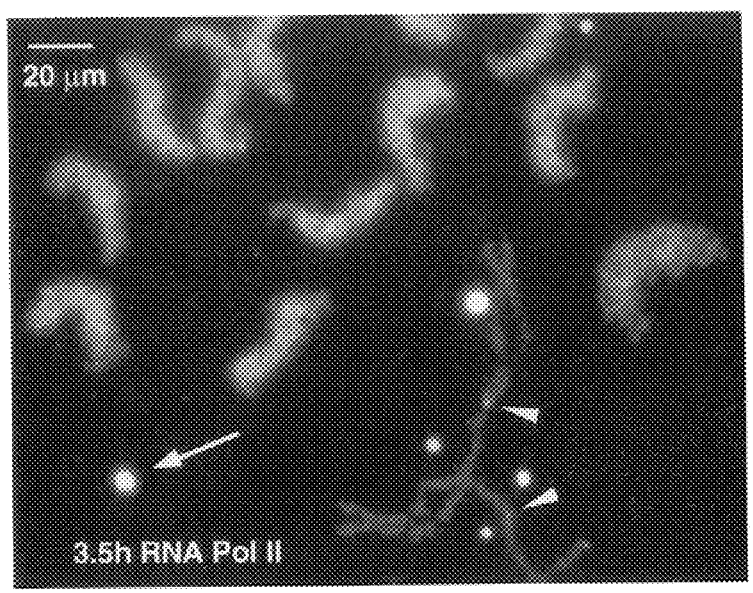
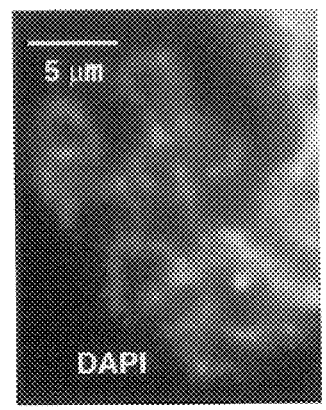
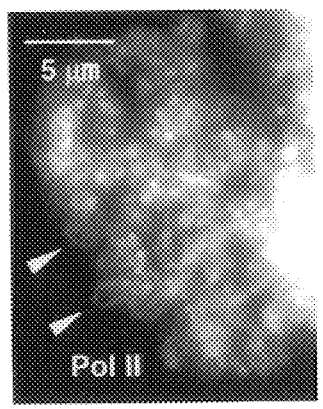
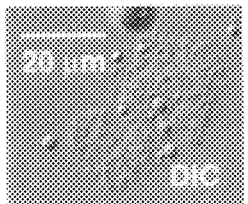
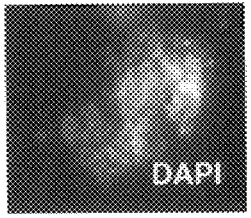
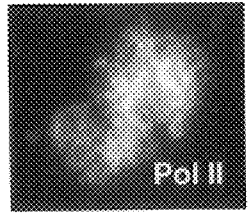
FIG. 2A
FIG. 2E
FIG. 2B   FIG. 2C   FIG. 2D   FIG. 2F

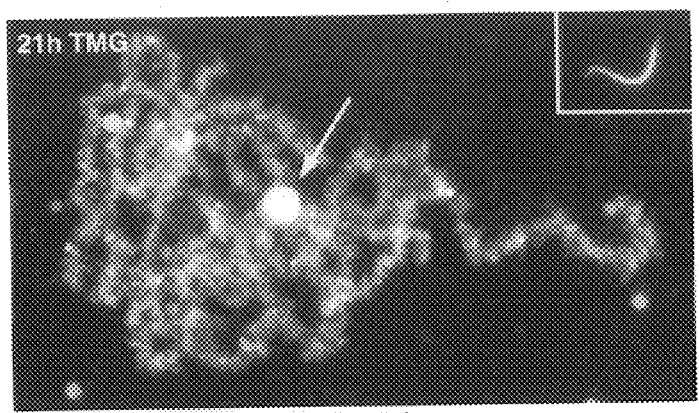
FIG. 3A
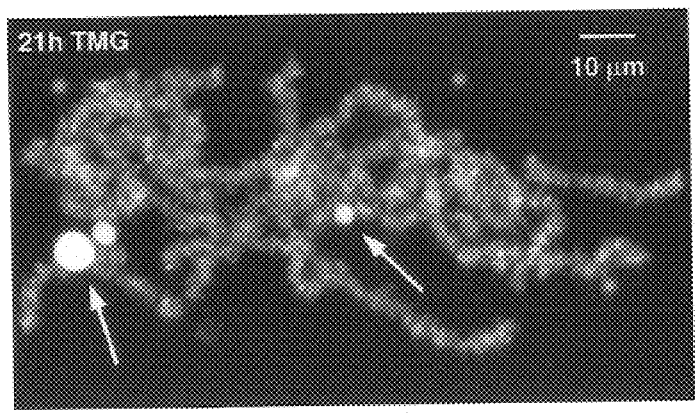
FIG. 3B
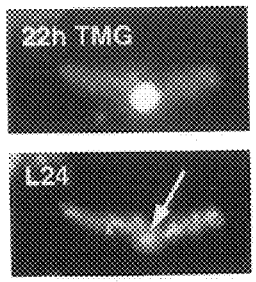
FIG. 3C
FIG. 3D
FIG. 3E
FIG. 3F
FIG. 3G
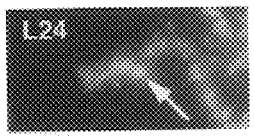
FIG. 3H

PRODUCTION OF LAMPBRUSH CHROMOSOME

This application claims the benefit of U.S. Provisional Application No. 60/066,103, filed Nov. 17, 1997.

GOVERNMENT RIGHTS

The U.S. Government has a paid-up license in this invention and the right in limited circumstances to require the patent owner to license others on reasonable terms as provided for by the terms of research grant GM-33397 awarded by the National Institute of General Medical Sciences.

BACKGROUND OF THE INVENTION

1. Field of the Invention

The present invention relates to a process for inducing a transcriptionally active chromosome (i.e., a "lampbrush" chromosome) from condensed chromatin or nuclei.

2. Description of the Related Art

More than 100 years ago, Flemming described giant chromosomes in the oocyte nucleus or germinal vesicle (GV) of the salamander *Ambystoma mexicanum*. His initial brief observations were soon followed by detailed investigations that established the existence of giant chromosomes in GVs of many animals, both vertebrate and invertebrate. Rückert named them lampbrush chromosomes (LBCs) because of their fancied resemblance to the brushes used for cleaning kerosene lamp chimneys.

Lampbrush chromosomes of amphibian oocytes are the largest known chromosomes, rivaled only by the giant polytene chromosomes of Drosophila and other flies. They are characterized by the presence of hundreds or thousands of transcriptionally-active regions that loop out laterally from the main axis of the chromosome. Each loop consists of one or a small number of active genes. Striking variations in the morphology and/or molecular composition of individual loops and of other landmarks along the main axis (e.g., centromeres, telomeres, axial granules, and the like) make it possible to map these chromosomes at the gene level by conventional light microscopy, using combinations of morphology, antibody binding, and in situ nucleic acid hybridization.

Although lampbrush chromosomes are found in a variety of organisms, they are conspicuously absent from many others or are not analyzable in some cases because of the small size of germinal vesicles in some organisms. For instance, it is still debatable whether typical lampbrush chromosomes occur in mammalian oocytes, including human oocytes, but even if they do, the germinal vesicle is too small to analyze such chromosomes by the techniques of the prior art.

The overall organization and functional significance of lampbrush chromosomes have been the subject of extensive experimentation and speculation (reviewed in Callan, 1986; Davidson, 1986). Because LBCs occur in oocytes during the growth period, they are in an arrested diplotene phase of meiosis I with homologous chromosomes held together at one or more chiasmata. Each homologue has a DAPI-positive axis of chromomeres, which correspond to transcriptionally-inactive regions where sisters are intimately associated. Numerous pairs of loops extend laterally from the chromomere axis; these consist of transcriptionally-active regions where sisters are completely independent of one another. Even at the light microscope level of analysis, loops are not of uniform thickness, but contain of one or more "thin-to-thick" regions, which correspond to transcription units. The electron microscope shows that the "thin-to-thick" morphology reflects the increasing length of nascent RNP fibrils along the transcription unit in the direction of transcription. This structure of LBCs reflects their transcriptionally active state.

Despite a wealth of detailed morphological and molecular information on lampbrush chromosomes, fundamental questions remain about their structure and especially about the significance of their highly active transcription. At one time their structure was regarded as unusual, but the discovery of looped chromatin domains in somatic nuclei (Paulson and Laemmli, 1977; Saitoh and Laemmli, 1993; Yokota et al., 1995) suggests that the lampbrush condition is a good model for chromosomes in general. However, the cis and trans factors which cause a condensed chromosome to assume the lampbrush condition had not been identified.

These and other questions about LBCs would be easier to address in a system in which the lampbrush state could be artificially induced and manipulated. In the present application, we disclose that condensed chromatin injected into a heterologous germinal vesicle gives rise within hours to distinctive transcriptionally-active LBCs. This system will be useful in assessing the relative importance of cis and trans acting factors in establishing the morphological and molecular attributes of LBCs. It should also permit analysis of transcriptionally-active chromosomes from organisms whose oocytes cannot be handled by current techniques or do not go through a typical lampbrush stage. Furthermore, LBCs from interphase nuclei exhibit a pattern of loops useful for cytogenetic analysis with higher resolution than interphase chromosomes painted by fluorescent in situ hybridization. Such loop patterns allow mapping, essentially at the single gene level.

SUMMARY OF THE INVENTION

In one embodiment of the invention, a process is provided of contacting a chromosome from sperm or other nuclei with the contents of a germinal vesicle of an oocyte to produce a transcriptionally active chromosome (i.e., a lampbrush chromosome). Examples of such are microinjection into an intact germinal vesicle, exposure to an extract of germinal vesicles or fractionated oocytes in a cell-free system, and incubation with isolated fractions of germinal vesicle contents. Preferably, the chromosome and the germinal vesicle are derived from organisms of different species (i.e., a heterologous process).

The chromosome-containing nuclei may be derived from sperm, other totipotent cells, interphase cells, somatic or differentiated cells, hematopoietic cells, benign or metastatic tumors, normal or transformed solid tissues, non-proliferating cells, and non-replicating cells. The source of the nuclei may be a vertebrate, such as a fish, mammal, hamster, mouse, rat, or human.

Germinal vesicles and oocytes are preferably from an amphibian (e.g., frog, newt, salamander, toad) but are not a preferred source of chromosomes. In the heterologous process, the chromosome produced has a morphology which resembles lampbrush chromosomes of the source of the germinal vesicle.

Disruption or removal of membranes, especially the nuclear envelope, surrounding the chromosome is preferred prior to contact with the germinal vesicle contents. Detergents, enzymes, mechanical disruption, or a combination thereof, may be used for removal of the membrane.

Another embodiment of the invention is providing the transcriptionally active chromosome (i.e., a lampbrush chromosome) produced by the invention on a solid substrate. Preferably, the chromosome produced is attached to a glass microscope slide or electron microscope grid.

The advantages of the invention include the ability to manipulate the conditions under which lampbrush chromosomes are produced, to provide chromosomes from interphase nuclei with distinctive loop patterns, and to produce such looped chromosomes from organisms or tissues which do not naturally contain lampbrush chromosomes.

BRIEF DESCRIPTION OF THE DRAWINGS

FIG. 1. (A) Demembranated sperm heads of *Xenopus laevis* prior to injection (DNA was stained with 4′,6-diamidino-2-phenylindole or DAPI). (B) Swollen sperm heads 5 min after injection into a Xenopus GV (DAPI stain). (C) The same field as panel B stained with mAb H14 against RNA polymerase II: sperm heads are negative, whereas a coiled body (sphere) stains brightly (arrowhead). (D) A sperm head 3 hr after injection into a GV (DAPI stain). (E) The same sperm head shows strong staining with mAb H14 against RNA polymerase II. (F) Sperm heads 3 hr after injection into a GV (DAPI stain). (G) The same field as panel F stained with mAb K121 against the trimethylguanosine cap of snRNAs: sperm heads are negative whereas B snurposomes are stained (arrowheads). (H) Sperm heads 3 hr after injection into a GV (DAPI stain). (I) The same field as panel H stained with mAB Y12 against the Sm epitope of snRNPs: sperm heads are negative whereas B snurposomes are stained (arrowheads).

FIG. 2. (A) A group of Xenopus sperm heads 3.5 hr after injection into a Xenopus GV, which have swollen extensively and stain strongly with mAb H14 against RNA polymerase II. An endogenous lampbrush chromosome is fused at its terminal granules to two other chromosomes (arrowheads). Several brightly staining coiled bodies (spheres) are also present (arrow). (B) DIC image of a single sperm head from the same GV. (C) DAPI stain reveals individual chromatids within the sperm head. (D) Staining with mAb H14 against RNA polymerase II gives a strong reaction in the sperm head. (E) Higher magnification of part of panel C showing DAPI-positive threads. (F) Individual polymerase II-reactive loops (arrowheads) can be seen in this enlargement of the same region from panel D.

FIG. 3. (A) and (B) Two Xenopus sperm heads 21 hr after injection into a Xenopus GV. Each has resolved into a loose cluster of chromosomes with most of the features of the endogenous LBCs. Stained with mAb K121 against the trimethylguanosine cap of the splicing snRNAs. The loops of the sperm LBCs stain strongly for snRNAs. Each cluster of chromosomes also displays one very large K121-reactive mass and several smaller masses (arrows). These almost certainly correspond to the similar masses that occur on bivalents #6, #8 and #14. (C) A single sperm LBC with a large K121-reactive mass attached near its center. The position of the mass and the relative size of this chromosome identify it as No. 14. (D) The same chromosome was double stained with serum L24 against protein xnf7 (Reddy et al., 1991). This antibody stains small inclusions in the mass (arrow) as well as most of the lampbrush loops, as it does on the endogenous LBCs. (E) DAPI staining of the same chromosome to show the axis of condensed chromomeres. (F) to (H) K121, L24, and DAPI staining of another example of what is probably sperm LBC No. 14, attached at one end to another chromosome. Arrow in panel G points to L24-reactive granules inside the mass.

Figure 4:
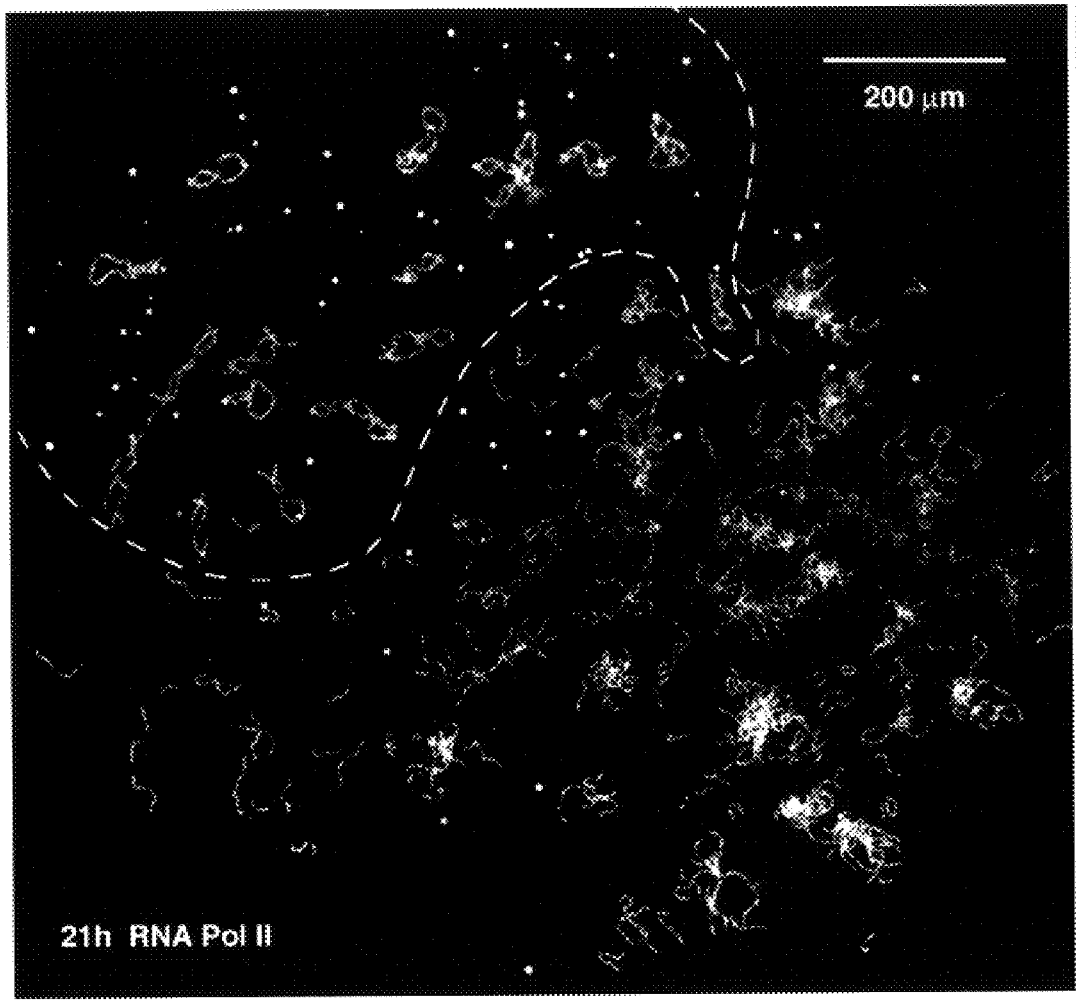
FIG. 4. Overview of the contents of a single Xenopus GV 21 hr after injection of Xenopus sperm heads. The sperm heads have been converted into loose clusters of chromatids or single chromatids that have the characteristic features of LBCs. This GV probably received 15–20 sperm heads. The 18 endogenous LBCs and most of the coiled bodies (spheres) occupy an area in the upper left part of the field (dashed line). Stained with mAb H14 against RNA polymerase II.

(Roth and Gall, 1987), which normally stains newt but not Xenopus LBC loops. Staining demonstrates that newt proteins were used to assemble the Xenopus LBC. Arrow indicates a "single-loop bridge" as described below. (H) The same field showing the chromomere axis of the chromosome (DAPI stain).

FIG. 9. (A) Xenopus sperm head one hour after injection into a Xenopus GV. The oocyte was incubated in actinomycin D (20 mg/ml) for one hour before injection and was returned to the drug after injection (DAPI stain). (B) The same sperm head stained with mAb H14, showing uptake of RNA polymerase II by the sperm even though transcription was inhibited. (C) Sperm head 1.5 hr after injection into an actinomycin-treated oocyte (DAPI stain). (D) The same sperm head stained with mAb K121 against trimethylguanosine, showing the absence of splicing snRNAs. (E) Sperm head 1.5 hr after injection into an actinomycin-treated oocyte (DAPI stain). (F) The same sperm head stained with mAb Y12, showing absence of Sm proteins. Arrowheads point to Y12-reactive B-snurposomes. (G) Highly contracted chromosome from the same GV that contained the sperm head shown in panels A and B (DAPI stain). (H) The same area stained with mAb H14, showing absence of chromosomal reaction except for the terminal granule (arrowhead). A coiled body (sphere) shows typical staining (arrow).

FIG. 10. (A) $^3$H-GTP was injected into the cytoplasm of a Xenopus oocyte and one hour later Xenopus sperm heads were injected into the GV. An autoradiograph of the GV contents made 7 hr later shows no label in a sperm head (arrow) but strong label in three nucleoli (arrowheads), indicative of rRNA transcription (1.5 d exposure). (B) Autoradiograph of labeled sperm LBCs 31 hr after injection of $^3$H-GTP and sperm heads as in panel A. Active transcription takes place on the loops of the sperm LBCs. A nucleolus (arrowhead) is blackened by silver grains (1.5 d exposure). (C) Oocytes were preincubated for 1 hr in actinomycin D (20 mg/ml), injected with $^3$H-GTP and sperm heads as in panel A, then returned to the drug. An autoradiograph of GV contents made 7 hr later shows no label in the sperm heads (arrows) or in the endogenous nucleoli (arrowhead) (1.5 d exposure). (D) A sperm LBC from an oocyte depleted for U2 snRNA, stained with serum L24 against xnf7 (Reddy, 1991). Loops are well stained, as are granules inside the large "mass" attached to the chromosome (arrowhead). (E) The chromosome in panel D stained with mAb K121 against trimethylguanosine. The loops show markedly reduced staining relative to untreated oocytes (compare FIG. 3), but the K121-reactive masses are not affected.

DESCRIPTION OF PREFERRED EMBODIMENTS

The present invention provides a method to convert highly condensed chromatin (e.g., such as is found in sperm heads) into giant transcriptionally-active lampbrush chromosomes, which can then be cytologically mapped and analyzed by a variety of molecular techniques, such as antibody binding for proteins and in situ hybridization for nucleic acids.

The process yields chromosomes on a microscope slide or other substrate that can be analyzed by morphology, autoradiography, histochemical staining, immunofluorescence, and other cytological or molecular techniques.

One basic process involves treating sperm heads with a detergent (such as lysolecithin) to disrupt or remove the investing membranes, including the nuclear envelope. The sperm heads are then microinjected into the giant nucleus or germinal vesicle (GV) of a living amphibian oocyte. During a period of 24–48 hours, the highly condensed, inactive chromosomes of the sperm head are released into the nucleoplasm of the GV, where they transform into giant transcriptionally-active "lampbrush" chromosomes.

A purpose of the invention is to produce microscopically indentifiable and/or genetically mappable giant chromosomes from sperm heads and other nuclei in which chromosomes are not normally visible or cytologically analyzable. Potential uses include:

a) analysis of sperm or another totipotent cell to assess the presence of chromosomal abnormalities or possible causes of infertility;

b) analysis of sperm cells from any organism, including human sperm, for determination of chromosome number or chromosome abnormalities that may be linked to infertility problems or genetic mutation;

c) analysis of normal chromosomes from any organism, including human, to gain information on the chromosomal location of genes, organization of genes, chromatin organization, functional genomics, or other chromosome elements (e.g., centromeres, telomeres, nongenic sequences, transcriptional control elements, and the like);

d) analysis of nuclei from a somatic or differentiated cell to assess the presence of chromosome abnormalities that might be associated with cancer or other diseases;

e) cytogenetic analysis at higher resolution than otherwise possible (e.g., genome mapping, karyotyping); and f) detailed mapping of chromosomes from organisms that normally do not have giant chromosomes (e.g., all mammals including humans).

Membranes surrounding sperm heads or other nuclei are partially or completely removed chemically (for example, by detergent, enzyme or a combination thereof), then the sperm heads may be microinjected into the nucleus or germinal vesicle (GV) of an oocyte. After a period of hours, the sperm heads or other nuclei spontaneously give rise to individually recognizable chromosomes (transcriptionally active "lampbrush" chromosomes).

Another process for practicing the present invention is to incubate condensed chromosomes from sperm or nuclei in an extract of GVs or fractionated oocytes. Such a cell-free system has been established to reconstitute DNA replication or the cell cycle (Lohka and Masui, 1983 and 1984), and further fractionation will identify trans factors involved in producing LBCs.

An extract can be prepared using subcellular fractionation (e.g., density buoyant or sedimentation centrifugation) to prepare a subcellular fraction which is enriched or depleted in lampbrush chromosome inducing activity. An extract or fraction may be further fractionated by protein purification techniques including precipitation (e.g., ammonium sulfate, heat denaturation, polyethylene glycol), chromatography (e.g., gel filtration, ion exchange, reversed phase, hydrophobic interaction, affinity), and electrophoresis (e.g., chromatofocusing, native or denatured polyacrylamide gel migration).

The present invention may convert chromosomes from interphase nuclei to LBCs, as it does with chromosomes from sperm heads. Methods to isolate nuclei from various tissues are known. Such isolated nuclei will be treated with detergent, an enzyme, or mechanical disruption to remove the nuclear envelope. They may then be injected into the GV of amphibian oocytes, where they would be expected to give rise to giant lampbrush chromosomes. In general, interphase nuclei are less condensed than sperm heads and may expand even more efficiently than the latter.

Advantages of using interphase nuclei are the greater number of tissues that can be examined, including both normal and tumor tissues. To determine the chromosomal constitution of tumors, it is necessary to culture their cells for days or weeks to obtain metaphase spreads. In many cases, it is impossible to induce the transformed cells to proliferate or the genome may undergo further chromosomal rearrangement in adapting to in vitro culture. Thus the present invention provides for chromosome analysis of otherwise intractable tissues.

Cells may be selected for a phenotype (e.g., chemical or drug sensitivity, cytokine or homone responsiveness) or segregated according to a detectable marker (e.g., separation or sorting on the basis of antibody or receptor interaction), and then analyzed for correlation to a particular genotype of the selected cell's LBCs.

Extracts of amphibian germinal vesicles may also be used in the present invention rather than intact germinal vesicles in living oocytes. An in vitro method for assembly of lampbrush chromosomes from sperm or other nuclei would eliminate the need for microinjection, thereby greatly simplifying the procedure and extending its usefulness. Furthermore, an in vitro system would permit a much deeper analysis of factors required for chromosome assembly. For instance, various native or genetically engineered proteins and/or nucleic acids can be readily added to an in vitro system, whereas they are often difficult or impossible to add to living cells. Similarly, various constituents can be removed from an in vitro extract by antibody inhibition or immunoprecipitation, antisense or ribozyme targeted RNA destruction, chemical inhibition (e.g., ATP or GTP hydrolysis, kinase or phosphatase inhibitors), fractionation, and other techniques much more readily than from living cells.

A goal of the present invention, therefore, is to produce transcriptionally-active lampbrush chromosomes from any type of nucleus or other chromosomal material in an in vitro extract whose composition can be manipulated at will.

All books, articles and patents cited in this specification are incorporated herein by reference in their entirety.

The following examples are meant to be illustrative of the present invention; however, the practice of the invention is not limited or restricted in any way by them.

We have examined the behavior of demembranated sperm heads when injected into the germinal vesicle (GV) of oocytes. Xenopus sperm heads injected into Xenopus GVs swelled immediately and within the first hours began to stain with an antibody against RNA polymerase II. Over time, each sperm head became a loose mass of chromosome-like threads, which by 24–48 hr resolved into individually recognizable lampbrush chromosomes (LBCs). LBCs derived from sperm were unreplicated single chromatids, but otherwise their morphology and immunofluorescent staining properties were strikingly similar to those of the endogenous lampbrush bivalents. They displayed typical transcriptionally-active loops extending from an axis of condensed chromomeres, as well as locus-specific "landmarks". Use of $^3$H-GTP and actinomycin demonstrated that transcription was not necessary for the initial swelling of the sperm heads and acquisition of RNA polymerase II, but was required for maintenance of the lampbrush loops. Splicing was not required at any stage during formation of sperm LBCs. When Xenopus sperm heads were injected into GVs of the newt Notophthalmus, the resulting sperm LBCs displayed very long loops with pronounced RNA polymerase II axes, like those of the endogenous newt LBCs; they stained with antibodies against newt-specific proteins. Other heterologous injections, including frog *Rana pipiens* and zebrafish *Danio rerio* sperm heads into Xenopus GVs, demonstrated that LBCs can be derived from taxonomically distant organisms. The GV system should identify both cis- and trans-acting factors needed to convert condensed chromatin into transcriptionally-active LBCs. It may also be useful in producing cytologically analyzable chromosomes from organisms whose oocytes do not go through a typical lampbrush phase or cannot be manipulated by current techniques.

MATERIALS AND METHODS

A general reference useful for background is *Xenopus laevis: Practical Uses in Cell and Molecular Biology* (Methods in Cell Biology, vol. 36, B. K. Kay and H. B. Peng, eds., Academic Press, San Diego, 1991).

Oocytes: A female *Xenopus laevis* was anesthetized with 0.1% methanesulfonate salt of 3-aminobenzoic acid ethyl ether (tricaine methane sulfonate or MS222, Sigma # A5040). A sample of ovary was removed surgically and held at 18–20° C. in a small petri dish of OR2 saline (Wallace et al., 1973). In some experiments the ovary sample was treated with crude collagenase from *Clostridium histolyticum*, which removes the outer layers of follicle cells and causes individual oocytes to come apart. Treatment was for 2–6 hr at room temperature in 0.2% collagenase (type II, Sigma # C6885) made up in $Ca^{++}$-free OR2. In other cases, individual oocytes or small clumps of oocytes with their follicle layers intact were separated with jeweler's forceps.

GV Spreads: Detailed instructions for studying lampbrush chromosomes of Xenopus were published earlier (Gall et al., 1991), but a few critical modifications now dramatically improve the quality of GV spreads (Gall, 1998). Injected oocytes were transferred one at a time to isolation medium (83 mM KCl, 17 mM NaCl, 6.5 mM $Na_2HPO_4$, 3.5 mM $KH_2PO_4$, 1 mM $MgCl_2$, 1 mM dithiothreitol, pH 7.0). The GV was removed with forceps and transferred within 20 sec to spreading medium (21 mM KCl, 4 mM NaCl, 1.6 mM $Na_2HPO_4$, 0.9 mM $KH_2PO_4$, 1 mM $MgCl_2$, 10 mM $CaCl_2$, 1 mM dithiothreitol, 0.1% paraformaldehyde, pH 7.0). The nuclear envelope was removed with jeweler's forceps and the nuclear gel was transferred with a pipette to a spreading chamber. If the procedure was carried out quickly, dispersal of the nuclear gel occurred within minutes and centrifugation could begin almost immediately. Slides were centrifuged in a special holder in an HS4 rotor (Sorvall) at 5000 rpm (4800 g), 4° C. for 30 min. GV spreads were fixed with 2% paraformaldehyde in PBS for one hour or longer.

Immunofluorescence: GV spreads were blocked with 10% horse serum in phosphate-buffered saline (PBS) for 15–30 min and then reacted with primary antibody for one hour. After a brief rinse in 3% horse serum, they were treated with a secondary antibody for another hour. Rabbit sera were diluted 1:200 in 10% horse serum, whereas mAbs were used as undiluted culture supernatant. Secondary antibodies were Cy3- or fluorescein-conjugated goat anti-mouse or goat anti-rabbit sera (Cappel/Organon Teknika, Durham, N.C.). Preparations were mounted in 50% glycerol containing 1 mg/ml of phenylenediamine (pH 9) and 1 mg/ml 4',6-diamidino-2-phenylindole (DAPI).

Sperm heads: Sperm heads were demembranated with lysolecithin as described by Gurdon (1976). Sperm heads of Xenopus laevis and Silurana (Xenopus) tropicalis were prepared from testes as described (Newmeyer and Wilson, 1991). Sperm of the mouse *Mus musculus* and the zebrafish *Danio rerio* were prepared in the same way; in the case of the mouse, mature sperm were obtained from the epididymis, whereas those of the zebrafish were squeezed from adult males. Sperm of the cricket *Acheta domesticus* were obtained by homogenizing 6–8 pairs of testes from adult insects in distilled water, which effectively destroys most cells but leaves mature and nearly mature sperm intact. The sperm were concentrated by centrifugation and then treated with lysolecithin as for the other species. In each case, sperm counts were made with a standard hemocytometer.

Oocyte injections: Some oocytes were partially defolliculated with collagenase before injection, whereas others were used without enzyme treatment. Defolliculated oocytes are easier to penetrate with the injection needle, but this advantage is offset by the time required for defolliculation and the somewhat greater fragility of treated oocytes. Before injection, oocytes were centrifuged at 1800 g for 20–30 min to bring the GV to the surface, where its position can be detected as a depigmented area. Glass needles were made from capillary tubing (0.5 mm i.d., 1.2 mm o.d.) using a vertical pipette puller (David Kopf Instruments, Tujunga, Calif.). Before use, the needle was siliconized and the tip was broken off with forceps to give an internal diameter of approximately 10 $\mu$m to 20 $\mu$m. The needle was filled from the back with mineral oil and the solution to be injected was then taken up through the tip. Injections of 4.8 $\mu$l or 9.6 $\mu$l were made under a dissecting microscope with a NANOJECT microinjection apparatus (Drummond Scientific Co., Broomall, Pa.), which employs a plunger to displace liquid in the needle. We found it advantageous to make injections soon after filling the needle with the sperm suspension. Test spottings onto a microscope slide showed that the number of ejected sperm decreased with time after filling, presumably due to settling of sperm heads and adherence to the side of the needle.

Transcription and Splicing: Transcription was monitored by injection of $^3$H-labeled GTP into the cytoplasm of oocytes. 250 $\mu$Ci of $^3$H-GTP (5.7 Ci/mM, Amersham) in 50% ethanol was evaporated to dryness and redissolved in 1.25 $\mu$l of H$_2$O. Approximately 1 $\mu$Ci (5 nl) was injected into each oocyte. At various times after injection, GV spreads were made and fixed in 2% paraformaldehyde as usual. They were dehydrated in an ethanol series and air dried from acetone. Unincorporated label was removed by treatment with 5% trichloroacetic acid at 4° C. for 5 min. After a second dehydration and drying from acetone, the slides were dipped in NTB2 autoradiographic emulsion (Eastman Kodak). Autoradiographic exposure was for 1.5 d, followed by development in D19 developer for 2 min. GV contents were stained through the emulsion with Coomassie blue (Gall et al., 1991). To inhibit splicing, 10 ng of a deoxyoligonucleotide complementary to U2 snRNA was injected with sperm into the GV (Pan and Prives, 1988; Tsvetkov et al., 1992). The oligo hybridizes with endogenous U2 snRNA in the GV, which is completely destroyed by RNase H activity within 1 to 4 hr. Preparations of LBCs made 24 hr after injection show unusually large loops that lack all detectable U2 snRNA) (Tsvetkov et al., 1992).

Injection of sperm heads

Initial experiments involved injection of demembranated *Xenopus laevis* sperm heads into *X. laevis* GVs of stage IV–V oocytes (1.0 mm to 1.2 mm diameter). In various experiments, the injected volume was 5–10 nl, nominally containing 1–5 sperm heads/nl, but the number of injected heads was often lower than calculated, probably due to adherence of the heads to the inside of the needle. At various times after injection, GVs were manually dissected from the oocytes, their contents were allowed to disperse in specially prepared well slides, and the slides were centrifuged to insure attachment of the GV contents to the glass substrate. We have now carried out several dozen injection experiments, each involving 20 to 60 oocytes. In a typical experiment, about 90% to about 95% of the injected oocytes appear normal after 24 hr, and of these from about 60% to about 90% received sperm heads in the GV. The remainder presumably represent cases where the needle missed the GV or sperm heads were not expelled from the needle.

Initial swelling of sperm heads

Demembranated Xenopus sperm heads as used for injection are worm-like structures roughly 20 $\mu$m in length, tapered toward both ends with a maximal diameter near the middle of about 1 $\mu$m (FIG. 1A). After injection into the GV, they were easily recognized by their morphology and their intense staining with the DNA-specific dye DAPI. The first sign of change in the sperm heads was swelling (FIGS. 1B–C), which took place within minutes, without formation of a membrane or envelope detectable by phase contrast or differential interference (DIC) microscopy (FIG. 2C). The timing of subsequent events was variable from experiment to experiment, possibly related to differences in oocytes from different females. In many cases the swollen sperm heads remained more or less unchanged during the first 3–6 hr (FIGS. 1D–I), whereas in other experiments there was marked decondensation and the first indication of LBC structure (FIG. 2).

For monitoring changes in the composition of sperm heads we have used three antibodies that detect transcription and splicing components of the nucleus: mAb H14 against RNA polymerase II (Pol II) (Bregman et al., 1995), mAb Y12 against the Sm proteins associated with splicing snRNPs (Lerner et al., 1981), and mAb K121 against the trimethylguanosine cap of snRNAs (Krainer, 1988). mAb H14 is particularly useful for the study of LBCs because it stains only the axis of the lateral loops, leaving the ribonucleoprotein (RNP) matrix unstained. In this way, one can follow the course of individual loops even in regions where there is considerable overlap. Among the extrachromosomal organelles in the GV, mAb H14 is highly specific for the coiled bodies (spheres), leaving essentially everything else unstained (FIGS. 1C and 2A). It is not known whether the staining of coiled bodies is due to RNA polymerase II or to a cross-reacting epitope. mAbs Y12 and K121 allow the identification of snRNPs; both of them stain the matrix of the loops (FIG. 3) and the snRNP-containing bodies in the GV referred to as B-snurposomes (Wu et al., 1991) (FIGS. 1G and I).

Sperm heads begin to stain with mAb H14 within the first few hours after injection (FIGS. 1D–E), presumably due to uptake of RNA polymerase II from stored reserves in the GV. This uptake is not accompanied by transcription and occurs even when transcription is inhibited by actinomycin. Splicing factors are not taken up initially, as shown by the absence of Y12 and K121 staining (FIGS. 1F–I). As the sperm heads continue to expand, they stain more and more intensely for RNA polymerase II (FIG. 2A). DAPI staining for DNA reveals the first indication of individual chromatids within these swollen heads (FIGS. 2C and E). Even at this early stage, careful examination reveals the presence of RNA polymerase II-reactive loops extending from the DNA (FIG. 2F, arrowheads). These loops signal the onset of RNA synthesis and the accumulation of nascent transcripts.

Appearance of definitive lampbrush structure

The sperm heads eventually resolved into loose clusters of fuzzy threads that closely resembled the endogenous LBCs (FIG. 3). Over time these clusters fell apart into individual chromosomes or small groups of chromosomes, which we refer to as "sperm LBCs". The sperm LBCs were easily recognizable, because they were unpaired and slightly shorter than the 18 endogenous bivalents in the same GV (FIG. 4). Sperm LBCs did not disperse evenly throughout the volume of the GV but remained together, presumably moving only slowly from the site of injection. In various experiments, from one to about 20 sperm heads were injected into a single GV. Within these limits, the system was not saturable, in the sense that sperm LBCs appeared similar in morphology and staining properties whether derived from one or many sperm heads.

Figure 5A:
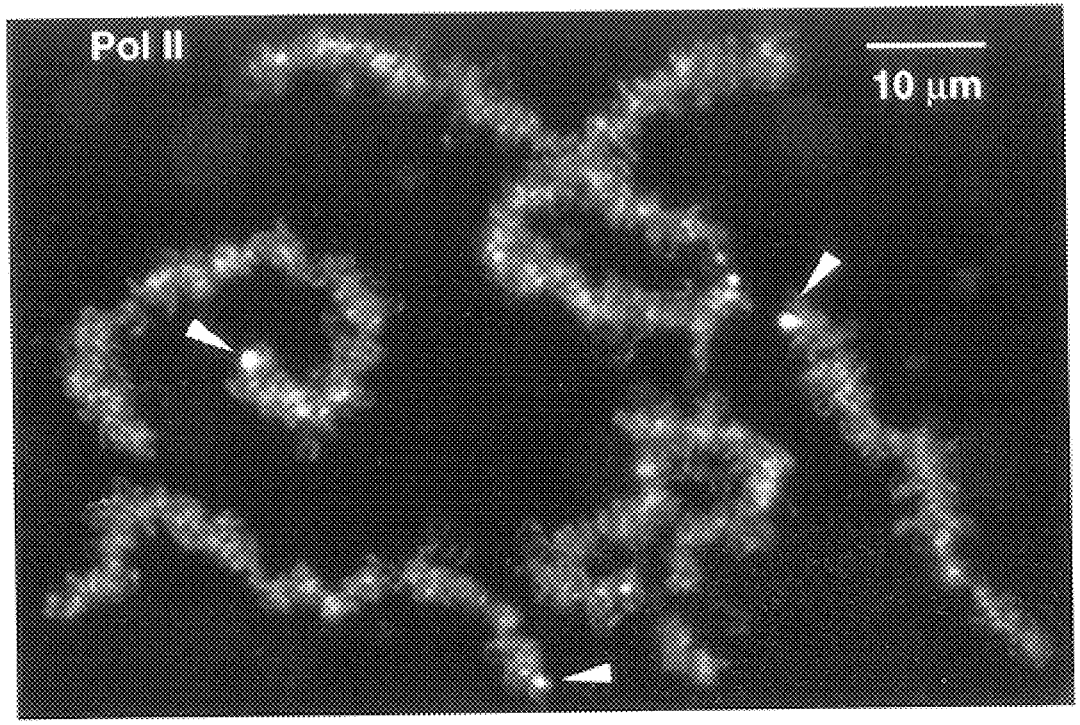
FIG. 5. (A) Higher magnification of several sperm LBCs from the GV shown in FIG. 4, stained with mAb H14 against RNA polymerase II. The overall fuzzy appearance of the chromosomes is due to staining of the axes of the lateral loops. In addition, mAb H14 stains the terminal granules (arrowheads) found at the end of the long arm of 15 of the 18 Xenopus LBCs. (B) A single sperm LBC at still higher magnification, stained with mAb H14. The arrowhead points to the terminal granule, arrows to loop axes (DNA axes covered with RNA polymerase II).
Figure 5B:
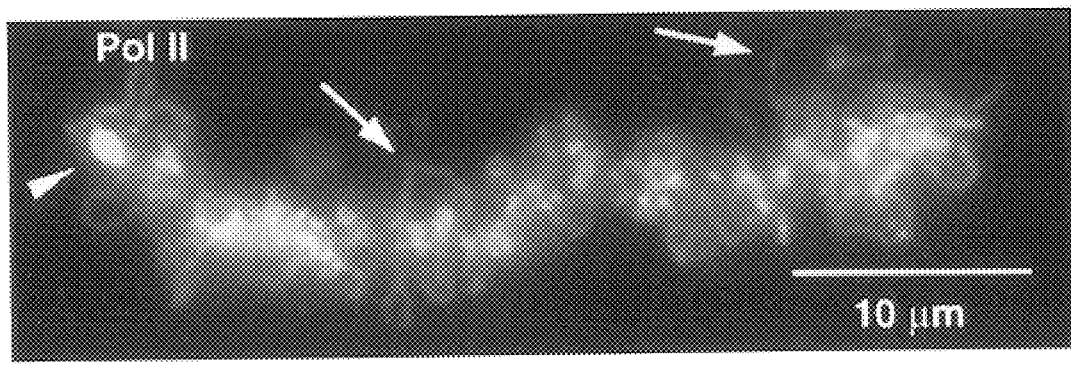

In overall structure, sperm LBCs closely resemble the endogenous chromosomes in the same nucleus. They each have a DAPI-positive chromomere axis (FIGS. 3E and H), which is less intensely stained than that of the endogenous LBCs, presumably reflecting the difference between a single chromatid and two closely paired sister chromatids. Loops on the sperm LBCs stained with antibodies against various proteins associated with nascent transcripts, such as L24 against xnf7 (Reddy et al., 1991) (FIGS. 3D and G), and they also contained splicing factors, as demonstrated by staining with Y12 and K121 (FIGS. 3A–C and F). The axis of each loop was well-delineated wtih mAb H14 against RNA polymerase II (FIG. 5B).

Sperm LBCs are complete chromosomes

The longest of the 18 lampbrush bivalents of *X. laevis* is just twice the length of the shortest and the remaining chromosomes form a closely graded series (Müller, 1974; Callan, 1987). The sperm LBCs are similarly graded in size with no particularly long or short members (FIGS. 4 and 5). Superficially, therefore, they look as if they might be derived from undefined fragments of sperm chromatin. However, closer inspection and comparison with the endogenous bivalents show that most of them are whole unbroken chromosomes.

Figures 6A, 6B, 6C:
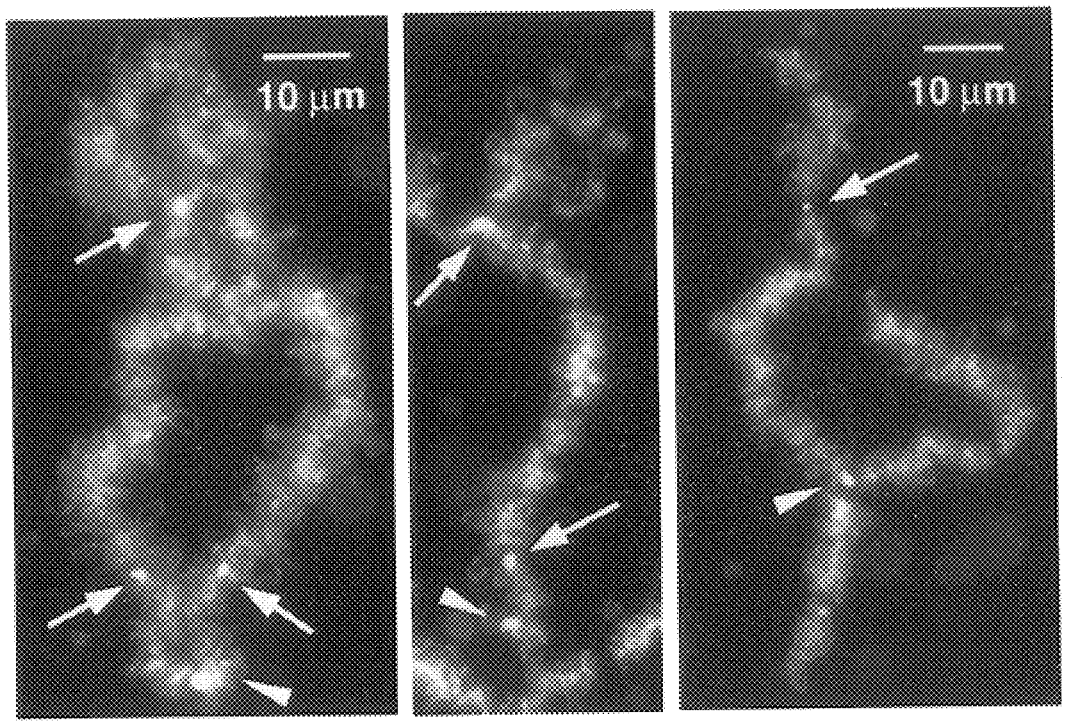
FIG. 6. (A) Bivalent # 11 is identifiable by a terminal granule at the end of its longer arm (arrowhead), and axial granules at positions 0.16 and 0.80 (arrows). In this example there is a single fused granule at position 0.80. The centromere lies immediately beyond the fused granule, but is not visible with this stain. The shorter arm has a characteristic diffuse structure. Stained with mAb H14 against RNA polymerase II. (B) Chromosome No. 11 derived from a sperm. The terminal granule (arrowhead), two axial granules (arrows), and the diffuse short arm are recognizable. (C) Another example of chromosome No. 11 derived from a sperm. The axial granule at 0.16 is not evident in this image, but the chromosome is reliably identified by the axial granule at 0.80 (arrow), the diffuse short arm, and the terminal granule (arrowhead), here fused to the terminal granules of two other chromosomes to give a triradiate figure.

Of the 18 bivalents, 15 possess a conspicuous terminal granule at the end of the long arm, referred to in earlier papers as a telomere (Callan, 1987). This granule contains the genes coding for 5S rRNA and stains intensely with mAb H14, although there is no direct proof that it contains RNA polymerase II. These granules tend to fuse with one another in various combinations. Nearly every GV has at least one bivalent in which the terminal granules of the two homologues are fused into a single granule (FIG. 6A), and fusions between the termini of non-homologous chromosomes are equally frequent (FIG. 2A, arrowheads). Casual inspection of sperm LBCs show that many also have one end capped by a terminal granule that stains with mAb H14 (FIGS. 5A–B). Non-homologous fusion between sperm LBCs are especially common, giving rise to multi-armed configurations that look superficially like branched chromosomes (FIG. 6C).

The strongest proof that sperm LBCs are whole chromosomes comes from identification of specific chromosomes. Among the most distinctive LBCs to identify is No. 14. Near the middle of this chromosome is a short region to which are attached oval or spherical masses that stain intensely with mAbs Y12 and K121. Such a mass is a conspicuous feature in each cluster of sperm LBCs (FIGS. 3A–B), and in many case chromosome No. 14 can be individually recognized (FIGS. 3C–H).

Chromosome No. 11 is also readily identified. In addition to a prominent terminal granule, it has two axial granules that also stain brightly with mAb H14 (FIG. 6A). The axial granule nearest the end of the long arm is the locus of the U2 snRNA genes and is often associated with a prominent pair of loops; the second axial granule lies immediately adjacent to the centromere. Highly characteristic of chromosome 11 is the loose organization of the short arm with almost no recognizable chromomeres and frequent double-loop bridges. FIGS. 6B and C show two examples of sperm LBCs that display the characteristics of chromosome No. 11. FIG. 6B all of the features just mentioned are recognizable, and in FIG. 6C the axial granule at the U2 locus is not obvious, but the chromosome is otherwise identifiable as No. 11. Additional examples of identifiable chromosomes will be pointed out in the section dealing with injection of heterologous sperm heads.

Sperm LBCs contain a single unreplicated chromatid

Each sperm contains a haploid number of unreplicated chromatids, 18 in the case of *X. laevis*. Consequently, each sperm LBC should consist of an unreplicated chromatid, unless DNA synthesis occurs after the sperm is injected. When sperm heads are incubated in Xenopus egg extract, they enter the S phase and carry out DNA synthesis, as shown by Lohka and Masui (1983). However, the S phase of an oocyte occurs in the interphase before the onset of meiosis, and there is no evidence for DNA synthesis in GVs at the lampbrush stage. Nevertheless, some caution is necessary in evaluating the DNA synthetic capacity of the GV, because an unusual amplification of rDNA does take place at pachytene in amphibian oocytes (Brown and Dawid, 1968; Gall, 1968).

Figure 8A:
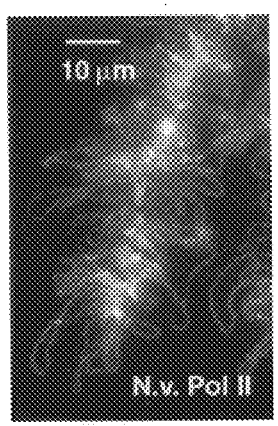
FIG. 8. (A) A small portion of a typical LBC from a GV of the newt *Notophthalmus viridescens,* stained with mAb H14 against RNA polymerase II. (B) The same field by DIC. Compared to a Xenopus LBC, the newt LBC has longer loops, more heavily textured and prominent loop matrix, and unusually distinct RNA polymerase II-reactive loop axes. In addition, newt LBCs are longer than Xenopus LBCs. (C) An LBC derived from a Xenopus sperm head that had been injected two days previously into a newt GV. Stained for RNA polymerase II. (D) The same field by DIC. Note how strongly this Xenopus LBC resembles a newt LBC except for length. (E) A Xenopus sperm LBC two days after injection of Xenopus sperm into a newt GV. Stained with serum L24 against xnf7 (Reddy et al., 1991). Only a few loops react strongly with this antibody. Note that the large loop (arrow) near the chromosome end is single, not paired like the loops in an oocyte LBC. This loop consists of two tandem transcription units, only one of which stains. (F) The same field by phase contrast. (G) A Xenopus sperm LBC two days after injection into a newt GV. Stained with mAb SE5
Figure 8B:
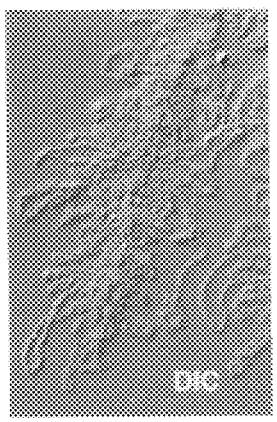
Figure 8C:
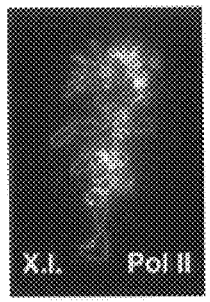
Figure 8D:
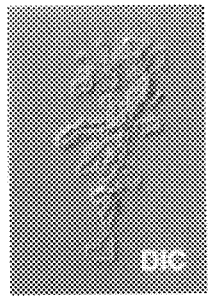
Figure 8G:
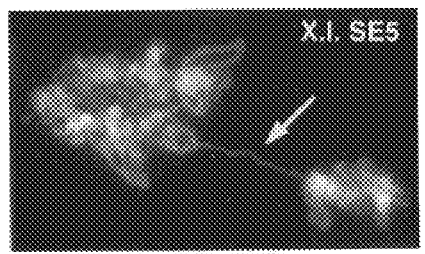
Figure 8E:
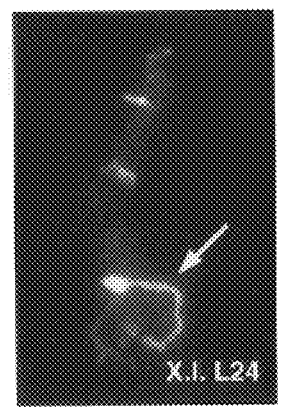
Figure 8F:
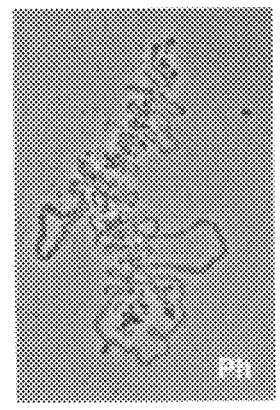
Figure 8H:
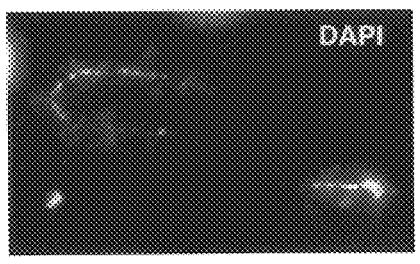

The existence of two chromatids in each homologue of a lampbrush bivalent was originally inferred from the paired nature of the lateral loops (discussed in Callan, 1986). If sperm LBCs consist of unreplicated chromatids, they should have unpaired loops. Although the majority of sperm LBC loops are too short and similar in appearance for evaluation, their unpaired condition is revealed under several circumstances. First, when a specific loop is recognizable because of size or unusual morphology, it is always single, never paired, as it would be in a typical bivalent (FIGS. 7A–D). Second, some loops can be stained specifically with antibodies. Again, these loops are single on sperm LBCs (FIGS. 8E–F). Third, when conventional LBCs are stretched, they display a phenomenon known as "double loop bridges" (Callan, 1955; Callan and Lloyd, 1960). A double loop bridge occurs when the bases of a pair of loops give way under tension; what were originally paired sister loops end up as parallel strands stretched out along the axis of the chromosome. Such double bridges have not been seen in the case of the sperm LBCs, but instead "single loop bridges" are relatively common (FIGS. 8G–H). These bridges show that a sperm LBC consists of a single chromatid.

Transcription and splicing

Figure 9A:
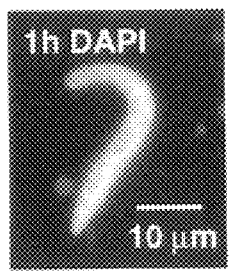
Figure 9B:
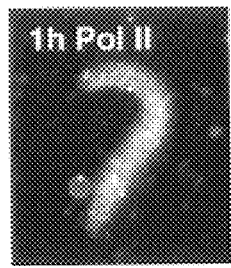
Figure 9C:
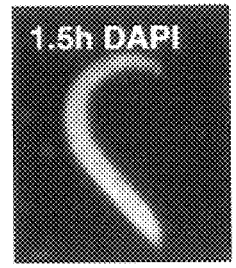
Figure 9D:
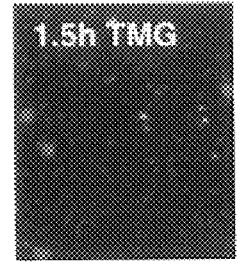
Figure 9E:
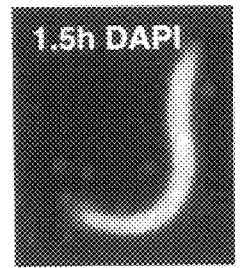
Figure 9F:
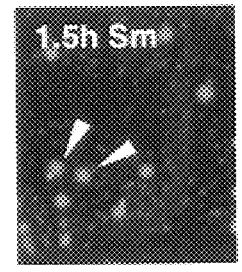
Figure 9G:
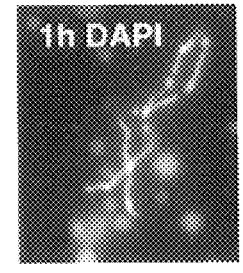
Figure 9H:
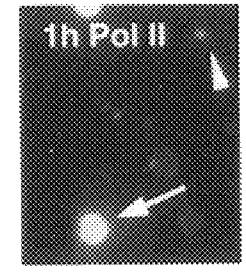
Figures 10A, 10B, 10C, 10D, 10E:
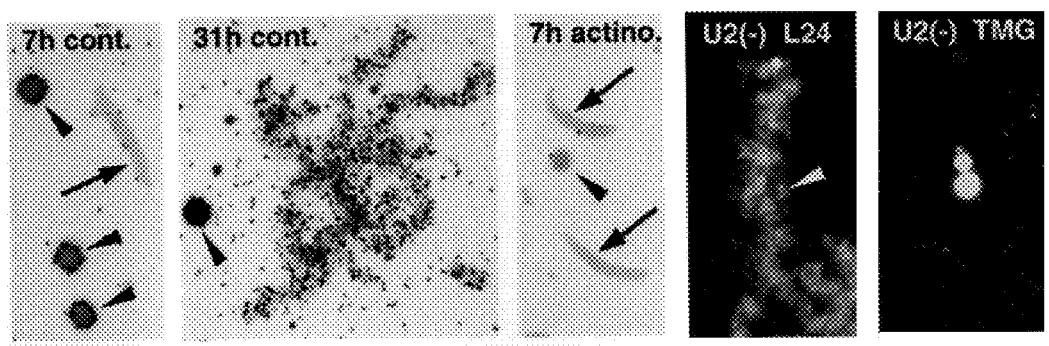

It has been demonstrated many times that lampbrush loops are actively engaged in RNA synthesis and that inhibition of transcription with actinomycin or alpha-amanitin leads to loss of loop RNP matrix and retraction of the loops (Izawa et al., 1963; Schultz et al., 1981; Callan, 1986) (FIG. 9G). To examine a possible relationship between transcription and early events in the formation of sperm LBCs, we injected $^3$H-GTP into the cytoplasm of oocytes, followed immediately by injection of sperm into the GV. Some oocytes were preincubated in actinomycin for about 1 hr beforehand and were returned to actinomycin after injection. In both sets of oocytes, sperm heads underwent initial swelling and by 1 hour stained intensely with mAb H14 against RNA polymerase II (FIGS. 9A–B). At this early time point, splicing components were not demonstrable in the sperm heads (FIGS. 9C–F). No further changes in the sperm heads were seen after longer incubation in actinomycin, whereas typical sperm LBCs eventually formed in oocytes held in OR2 saline. In oocytes held in OR2 saline for 7 hr after injection of sperm and $^3$H-GTP, nucleoli and endogenous chromosomes were strongly labeled, whereas the swollen sperm heads were unlabeled (FIG. 10A). $^3$H-GTP was not incorporated into any nuclear structures in the actinomycin-treated oocytes (FIG. 10C). Thus the initial stage of sperm enlargement and accumulation of RNA polymerase II take place in the absence of transcription. Oocytes examined a day later displayed well-formed sperm LBCs, which by this time were actively transcribing (FIG. 10B).

Earlier experiments with antisense oligodeoxynucleotides showed that transcription on LBCs can take place in the absence of U2 snRNA and thus does not require concomitant splicing (Tsvetkov et al., 1992). We have carried out a similar experiment that demonstrates the assembly of sperm LBCs in oocytes in which the splicing machinery was disrupted. FIGS. 10D and E show a sperm LBC from an oocyte injected 2 d earlier with sperm heads and with an oligodeoxyribonucleotide against U2 snRNA. This sperm LBC displays two features characteristic of U2-depleted GVs: the loops are unusually prominent and they show reduced staining with mAb K121. Because the targeted U2 snRNA was destroyed within the first four hours or less after injection (Tsvetkov et al., 1992), this experiment demonstrates that sperm LBCs can form in the absence of splicing.

In summary, the initial stage of sperm enlargement and accumulation of RNA polymerase II normally occurs without transcription and can take place even when transcription is inhibited by actinomycin. Whether transcription is necessary for the emergence of cytologically recognizable chromosomes from the sperm head has not been determined, but the maintenance of typical lampbrush loops does depend on transcription. Neither formation nor maintenance of sperm LBCs requires concomitant splicing.

Heterologous injections

We have carried out several experiments in which demembranated sperm heads of one species were injected into the GV of another. Such experiments can begin to distinguish cis from trans factors in the assembly of LBCs; that is, to assess the relative contributions of sperm chromatin, proteins, and other factors provided by the host GV.

Figure 7A:
FIG. 7. (A) to (D) Phase contrast images of four examples of the same sperm LBC derived from *Rana pipiens* sperm heads injected two days previously into a Xenopus GV. Near one end of this chromosome is an unusually large loop with a prominent granule at its base (arrowheads). Note that the loop is single, as expected for an unreplicated chromatid. (E) Same field as panel D, DAPI stained to show the prominent DNA axis. (F) A sperm LBC two days after injection of zebrafish *Danio rerio* sperm heads into a Xenopus GV. Stained with mAb K121 against trimethylguanosine. Arrowheads point to two loops with unusually heavy matrix.
Figure 7B:
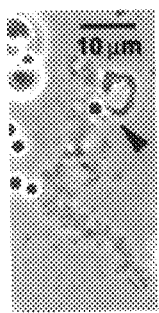
Figure 7C:
Figure 7D:
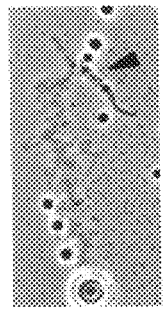
Figure 7E:
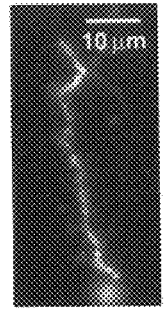

Sperm of Silurana (=Xenopus) tropicalis were injected into X. laevis GVs. Sperm LBCs derived from S. tropicalis appeared quite similar to those from homologous X. laevis injections. Because S. tropicalis has only 10 chromosomes in its haploid set, specific chromosomes were easier to identify, providing additional evidence that sperm LBCs are whole chromosomes. Sperm of the leopard frog Rana pipiens were also injected into X. laevis GVs. Again, the resulting sperm LBCs closely resembled the endogenous LBCs in both length and general morphology, and specific chromosomes could be recognized (FIGS. 7A–D). When examined by DAPI staining (FIG. 7E), the chromomere axes of the sperm LBCs were more prominent than those of the endogenous X. laevis bivalents, even though the comparison is between single and paired chromatids. The strong DAPI stain probably reflects the fact that R. pipiens has fewer chromosomes than X. laevis (n=13 vs. n=18), yet has a larger genome ($6.8\times10^9$ bp vs. $2.8\times10^9$ bp), so that the "average" chromatid of R. pipiens contains about three times as much DNA as an "average" chromatid from X. laevis.

The similarity of the loops on the R. pipiens sperm LBCs to those on the endogenous bivalents was unexpected. LBCs of R. pipiens within their own oocytes display larger loops, and we had been prepared to see more prominent loops on the sperm LBCs; that is, we had expected the origin of the sperm chromatin to have a greater effect on the morphology of the resulting LBCs.

Figure 7F:
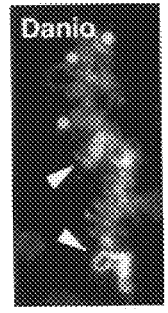

When sperm of the zebrafish Danio rerio were injected into X. laevis GVs, the resulting LBCs resembled the endogenous X. laevis bivalents in general morphology, although they were much shorter. The Danio chromosome in FIG. 7F was the longest one observed. Because Danio has a haploid number of 25 and a genomic DNA content of $1.7\times10^9$ bp, the "average" zebrafish chromatid has about 0.44 times the DNA of an "average" Xenopus chromatid.

Unexpected results were obtained when we injected X. laevis sperm into GVs of the newt Notophthalmus viridescens. The difference in morphology between Xenopus and newt LBCs is considerable, the lampbrush loops of the newt being among the largest known (FIGS. 8A–B). We were surprised to find that X. laevis sperm LBCs in GVs of N. viridescens resembled the endogenous newt chromosomes to a remarkable degree, except for their much shorter overall length. The resemblance involved three features of the loops: length, morphology of the RNP matrix, and prominence of the polymerase II axis. The most obvious similarity is in the length of the loops, which is greater than that normally seen on X. laevis chromosomes (cf. FIGS. 8C–H with FIGS. 5–6). Many loops were 30 $\mu$m to 40 $\mu$m in length, although on average they were not so long as those on the endogenous newt chromosomes. The RNP matrix of the sperm LBC loops is both abundant and varied in morphology like that of newt LBCs (FIGS. 8D and F). Similar variations in loop morphology occur on endogenous X. laevis LBCs but are less striking. A conspicuous feature is the staining of the loop axis with mAb H14 against RNA polymerase II. In normal newt LBCs and in X. laevis sperm LBCs in the newt GV, this axis is usually prominent (FIGS. 8A and C), whereas in normal X. laevis LBCs it is less conspicuous (FIG. 6A).

We used two newt-specific antibodies to examine the proteins associated with X. laevis sperm LBCs in the newt GV. mAb A33 detects a zinc-finger protein (A33) originally described from Pleurodeles waltl (Lacroix et al., 1985; Bellini et al., 1995), and mAb SE5 detects an unrelated protein (SE5) from N. viridescens (Roth and Gall, 1987). Both antibodies stain the RNP matrix of most but not all loops on the LBCs of N. viridescens, whereas neither reacts with the normal LBCs of X. laevis. However, in injection experiments, both stained X. laevis sperm LBCs indistinguishably from the endogenous N. viridescens chromosomes in the same GV. This observation demonstrates that newt proteins are used for the assembly of X. laevis sperm LBCs in newt GVs.

Other heterologous injection experiments have been carried out with some success. Lysolecithin-treated sperm heads from the mouse Mus musculus and the cricket Acheta domesticus were injected into GVs of X. laevis. The sperm heads of both species underwent an initial swelling and began to stain with mAB H14. However, in neither case did individual chromosomes become visible, although a few short loops extended from some of the mouse nuclei.

Samples of the same sperm heads formed typical in vitro nuclei after 30–60 min incubation in Xenopus egg extract, suggesting that competence in the latter assay is not a sufficient criterion for competence in the GV system.

We have shown that typical transcriptionally-active lampbrush chromosomes can be assembled from sperm chromatin when demembranated sperm heads are injected into the GV of intact oocytes. About 15 years ago, Lohka and Masui showed that such sperm heads transform into essentially normal pronuclei when incubated in an extract of Xenopus eggs (Lohka and Masui, 1983 and 1984), and the egg extract system has since been used to investigate many aspects of DNA replication and the cell cycle. The GV and egg extract systems are fundamentally different. In the egg extract, demembranated sperm chromatin becomes surrounded by a nuclear envelope and gives rise to a transcriptionally-silent nucleus that may subsequently undergo DNA replication and enter mitosis. In contrast, the same demembranated sperm chromatin remains freely exposed to the surrounding milieu of the GV does not undergo replication, and transforms into separate, transcriptionally-active giant chromosomes.

It has been documented that amphibian GVs contain large quantities of stored materials destined for the early embryo, including transcription and splicing factors. These factors allow the GV to transcribe injected DNA templates and to process the resulting RNA. GV extracts have been used to support transcription in vitro, as in the extensive studies of Brown and his colleagues on 5S RNA. Aqueous GV extracts have been of limited use for the study of polymerase II transcription, although GVs isolated under oil, and therefore retaining soluble co-factors, support efficient transcription from U1 snRNA templates. In early experiments by Gurdon, various types of somatic nuclei were injected into both cytoplasm and GVs of Xenopus oocytes, and the subsequent morphological and transcriptional events examined in considerable detail. Nuclei injected into the GV swelled and became transcriptionally active, while retaining an apparently intact nuclear envelope (Gurdon, 1976). Lampbrush chromosomes were not detected in these nuclei.

The present invention shows that maximally condensed chromatin can transform into LBCs in less than a day in the GV of a relatively mature oocyte (Dumont stage IV–V). Sperm heads acquire RNA polymerase II almost immediately after injection. After an initial period of swelling, transcription begins and additional factors are recruited to the nascent transcripts, including snRNPs. Several times as much chromatin can be converted as is normally present in the GV, and the process uses host proteins. These features underscore the importance of factors known to be stored in the GV, such as RNA polymerase II, hnRNPs, snRNPs, histones, and nucleoplasmin. Among other things, these stored factors are used in the conversion of DNA to chromatin during early embryogenesis and in the initiation of transcription after the mid-blastula transition. Normal lampbrush chromosomes show that the transcriptional machinery is functional in the GV, and the sperm injection experiments show that inactive chromatin can be activated for transcription.

The final form of LBCs derived from sperm chromatin must be influenced by features of the chromatin itself, as well as by factors in the GV where the transformation takes place. It might be expected that *X. laevis* sperm chromatin in a GV of *X. laevis* gives rise to LBCs that are indistinguishable from the endogenous LBCs. On the other hand, the results of the heterologous processes disclosed above are unexpected. It was known that some organisms, like salamanders and some frogs, have enormous LBCs with very long loops, whereas others, like Xenopus, have intermediate sized chromosomes with modest loops, and still others have very short chromosomes with barely detectable loops. These differences correlate reasonably well with the genomic DNA content or C value of the various organisms.

However, if overall chromosome length correlates with C value, why should loop length do so as well if loops simply correspond to one or a small number of transcription units? The explanation usually given is based on the existence of readthrough transcription at the lampbrush stage (Gall et al., 1983). In its simplest form, the reasoning is that the transcription unit includes all of the spacer between genes, and on average the length of spacers must increase with C value; therefore, transcription units will be longer in organisms with high C values. This model places almost all emphasis on cis elements and predicts that the sperm of a given organism should form similar LBCs regardless of the GV into which it is placed. However, our results with heterologous injections—particularly *X. laevis* sperm in the Notophthalmus GV, which give rise to chromosomes that look remarkably like newt LBCs—argue that trans factors play a significant role. This conclusion will require modification of the relatively simple model of LBC morphology based on overall DNA content.

To examine factors important in the assembly of LBCs, it will be necessary to add and subtract components from the GV contents. Antisense oligonucleotides can be used effectively to degrade RNA in the GV (Prives and Foukal, 1991). Earlier we used knockout of U2 snRNA to show that LBC transcription does not require concomitant splicing (Tsvetkov et al., 1992), and the same holds true for the transformation of sperm chromatin into LBCs. Depletion or addition of proteins is more problematic, although injection of antibodies into the GV has been used with some success (Bona et al., 1981; Scheer et al., 1984). It would be highly desirable to have an in vitro system for assembly of LBCs comparable to the egg extract for assembly of interphase nuclei. Efforts will be made first to repeat our experiments with GVs isolated under oil (Paine et al., 1992), and if these are successful, to prepare cell-free extracts from GVs or oocytes that will support the transformation of sperm into LBCs.

The present invention has been described for use with a variety of sources of chromosomes and germinal vesicles. Sources of germinal vesicles exemplified herein include frogs and newts. Chromosome-containing nuclei were obtained from, for example, frog, mouse, zebrafish and cricket tissue. The invention is contemplated for use with numerous other sources of germinal vesicles and chromosome-containing nuclei. In particular, human germinal vesicles and/or human chromosome sources are expected to produce transcriptionally active lampbrush chromosomes from condensed chromatin or nuclei according to the invention.

While the present invention has been described in connection with what is presently considered to be practical and preferred embodiments, it is understood that the present invention is not to be limited or restricted to the disclosed embodiments but, on the contrary, is intended to cover various modifications and equivalent arrangements included within the spirit and scope of the appended claims.

Thus it is to be understood that variations in the described invention will be obvious to those skilled in the art without departing from the novel aspects of the present invention and such variations are intended to come within the scope of the present invention.

REFERENCES

Bellini et al. (1995) J. Cell Biol., 131, 563–570.
Bona et al. (1981) J. Mol. Biol., 151, 81–89.
Bregman et al. (1995) J. Cell Biol., 129, 287–298.
Brown and Dawid (1968) Science, 160, 272–280.
Callan (1955) In: *Symposium of the 8th Congress of Cell Biology,* Noordhoff, IUBS Ser B21: 89–109.
Callan and Lloyd (1960) Philos. Trans. R. Soc. Lond. B. Biol. Sci., 243, 135–219.
Callan (1986) Mol Biol Biochem Biophys, 36, 1–252.
Callan (1987) Chromosoma, 95, 236–250.
Davidson (1986) *Gene Activity in Early Development,* 3rd ed., Academic Press.
Gall (1968) Proc. Natl. Acad. Sci. USA, 60, 553–560.
Gall et al. (1983) In: *Gene Structure and Regulation in Development,* (Subtelny and Kafatos, eds.) Alan R. Liss, 137–146.
Gall et al. (1991) Methods Cell Biol., 34, 149–166.
Gall (1998) In: *Cell Biology: A Laboratory Manual,* (Spector et al., eds.), Cold Spring Harbor Laboratory Press, 3.1–3.3.
Gurdon (1976) J. Embryol. Exp. Morph., 36, 523–540.
Izawa et al. (1963) Proc. Natl. Acad. Sci. USA, 49, 544–551.
Krainer (1988) Nucleic Acids Res., 16, 9415–9429.
Lacroix et al. (1985) Chromosoma, 92, 69–80.
Lerner et al. (1981) Proc. Natl. Acad. Sci. USA, 78, 2737–2741.
Lohka and Masui (1983) Science, 220, 719–721.
Lohka and Masui (1984) J. Cell Biol., 98, 1222–1230.
Müller (1974) Chromosoma, 47, 283–296.
Newmeyer and Wilson (1991) Methods Cell Biol., 34, 607–634.
Paine et al. (1992) BioTechniques, 13, 238–245.
Pan and Prives (1988) Science, 241, 1328–1331.
Paulson and Laemmli (1977) Cell, 12, 817–828.
Prives and Foukal (1991) Methods Cell Biol., 34,.
Reddy et al. (1991) Dev. Biol., 148, 107–116.
Roth and Gall (1987) J. Cell Biol., 105, 1047–1054.
Saitoh and Laemmli (1993) Cold Spring Harbor Symp. Quant. Biol., 58, 755–765.
Scheer et al. (1984) Cell, 39, 111–122.
Schultz et al. (1981) Chromosoma, 82, 171–187.
Tsvetkov et al. (1992) Molec. Biol. Cell, 3, 249–261.
Wallace et al. (1973) J. Exp. Zool., 184, 321–333.
Wu et al. (1991) J. Cell Biol., 113, 465–483.
Yokota et al. (1995) J. Cell Biol., 130, 1239–49.

What is claimed is:

1. A method of producing giant transcriptionally active lampbrush chromosomes, comprising:
   treating a source of highly condensed inactive chromosomes to partially or completely remove surrounding membranes;
   contacting demembranated inactive chromosomes with the contents of a germinal vesicle of an oocyte; and
   incubating the inactive chromosomes and germinal vesicle contents for a period of time sufficient to produce transcriptionally active, individually recognizable lampbrush chromosomes.

2. A method according to claim 1, wherein said source of highly condensed inactive chromosomes is obtained from sperm.

3. A method according to claim 1, wherein said source of highly condensed inactive chromosomes is obtained from an interphase nucleus.

4. A method according to claim 1, wherein membranes surrounding the source of inactive chromosomes are removed chemically by detergents, enzymes or a combination thereof.

5. A method according to claim 1, wherein membranes surrounding the source of inactive chromosomes are removed mechanically.

6. A method of identifying trans factors involved in forming lampbrush chromosomes produced according to claim 1, wherein the inactive chromosomes are incubated in an in vitro cell-free extract of germinal vesicles or fractionated oocytes.

7. A method according to claim 1, wherein the process is heterologous, such that the highly condensed inactive chromosomes are from a different organism than the germinal vesicle of an oocyte.

8. A method according to claim 7, wherein the heterologous process comprises injecting demembranated sperm heads of one species into the germinal vesicle of another species.

9. The method of claim 8, wherein said method further comprises staining the chromosomes to assess the relative contributions of sperm chromatin and factors provided by the germinal vesicle.

10. A method according to claim 7, wherein the source of inactive chromosomes is a an organism selected from the group consisting of *Xenopus laevis, Silurana tropicalis, Rana pipiens, Mus musculus, Acheta domestics* and *Danio rerio.*

11. A method according to claim 7, wherein the germinal vesicle is from an organism selected form the group consisting of *Xenopus laevis,* and *Notophthalmus viridescens.*

12. A method analyzing chromosomes for abnormalities, comprising:
   contacting inactive chromosomes with the contents of germinal vesicles of an oocyte;
   incubating the inactive chromosomes and germinal vesicle contents for a period of time sufficient to produce transcriptionally active, individually recognizable lampbrush chromosomes; and
   subjecting the transcriptionally active individually recognizable lampbrush chromosomes to cytogenetic analysis.

13. A method according to claim 12, wherein the cytogenetic analysis is selected from the group consisting of genome mapping, karyotyping, gene organization and functional genomics.

14. A method for producing a transcriptionally active lampbrush chromosome, comprising:
   (a) providing at least one chromosome obtained from a species;
   (b) contacting said chromosome with an amount of germinal vesicle contents of at least one oocyte, wherein said oocyte is from a different species than said species from which the chromosome is obtained; and
   (c) incubating said chromosome with said amount of germinal vesicle contents for a time period, wherein said amount is effective to and said time period is sufficient to produce at least one transcriptionally active lampbrush chromosome.

15. A method according to claim 14, wherein said germinal vesicle contents are obtained by preparing an extract of germinal vesicles.

16. A method according to claim 14, wherein said germinal vesicle contents are obtained by fractionating germinal vesicles.

17. A method according to claim 14, wherein said germinal vesicle contents are obtained by purifying proteins from germinal vesicles.

18. A method according to claim 14, wherein said chromosome is obtained from a species that does not normally have giant chromosomes and said oocyte is obtained from an amphibian species.

19. A method for cytogenetic analysis by producing a transcriptionally active lampbrush chromosome according to claim 14, and then further comprising recognizing at least one individual transcriptionally active lampbrush chromosome and subjecting at least one transcriptionally active lampbrush chromosome to cytogenetic analysis.

20. A solid substrate and a transcriptionally active lampbrush chromosome attached thereon produced by the method according to claim 14, wherein said chromosome is obtained from a species that does not normally have giant chromosomes.

21. A method for producing a chromosome with transcriptionally-active regions that loop laterally from its main axis, comprising:
 (a) providing at least one chromosome obtained from condensed chromatin of a species;
 (b) contacting said chromosome with an amount of germinal vesicle contents of at least one oocyte, wherein said oocyte is from a different species than said species from which the chromosome is obtained; and
 (c) incubating said chromosome with said amount of germinal vesicle contents for a time period, wherein said amount is effective to and said time period is sufficient to produce at least one chromosome with transcriptionally-active regions that loop laterally from its main axis.

22. A method according to claim 21, wherein said germinal vesicle contents are obtained by preparing an extract of germinal vesicles.

23. A method according to claim 21, wherein said germinal vesicle contents are obtained by fractionating germinal vesicles.

24. A method according to claim 21, wherein said germinal vesicle contents are obtained by purifying proteins from germinal vesicles.

25. A method according to claim 21, wherein said chromosome is obtained from a species that does not normally have giant chromosomes and said oocyte is obtained from an amphibian species.

26. A method for cytogenetic analysis by producing a transcriptionally-active chromosome according to claim 21, and then further comprising recognizing at least one individual transcriptionally-active chromosome and subjecting at least one transcriptionally-active chromosome to cytogenetic analysis.

27. A solid substrate and a transcriptionally-active chromosome attached thereon produced by the method according to claim 21, wherein said chromosome is obtained from a species that does not normally have giant chromosomes.

* * * * *